US007112555B1

(12) United States Patent
Lienart et al.

(10) Patent No.: US 7,112,555 B1
(45) Date of Patent: Sep. 26, 2006

(54) USE OF GLYCURONIC POLYSACCHARIDES AND OLIGOSACCHARIDES AS PHYTOSANITARY PRODUCTS AND/OR FERTILISER

(75) Inventors: Yvette Lienart, Uriage (FR); Alain Heyraud, Veurey-Vorolze (FR); Olivier Sevenou, Kegworth (GB)

(73) Assignee: Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 10/018,884

(22) PCT Filed: Jun. 23, 2000

(86) PCT No.: PCT/FR00/01761

§ 371 (c)(1),
(2), (4) Date: Apr. 17, 2002

(87) PCT Pub. No.: WO01/00025

PCT Pub. Date: Jan. 4, 2001

(30) Foreign Application Priority Data

Jun. 25, 1999 (FR) .................. 99 08135

(51) Int. Cl.
*A01N 43/02* (2006.01)
*A01N 43/16* (2006.01)
*C07G 17/00* (2006.01)

(52) U.S. Cl. .............. 504/291; 504/292; 536/1.11; 536/3; 536/4.1; 536/115; 536/120; 536/123.1; 536/123.13

(58) Field of Classification Search .............. 536/1.11, 536/3, 4.1, 120, 115, 123.1, 123.13; 504/291, 504/292
See application file for complete search history.

(56) References Cited

U.S. PATENT DOCUMENTS 4,226,855 A * 10/1980 Shigematsu et al. .......... 514/21
4,993,185 A * 2/1991 Adachi et al.
5,588,254 A * 12/1996 Adachi et al.
5,952,308 A * 9/1999 Nakanishi et al.

FOREIGN PATENT DOCUMENTS

| DE | 33 38 689 A1 | | 5/1985 |
|----|----|----|----|
| FR | 2 605 185 | | 4/1988 |
| FR | 2 688 222 | | 9/1993 |
| FR | 2688222 | * | 9/1993 |
| JP | 04 335839 A | | 11/1992 |
| JP | 4335839 | * | 11/1992 |
| JP | 05 316997 A | | 12/1993 |
| JP | 06 205687 A | | 7/1994 |
| JP | 07 274725 A | | 10/1995 |
| JP | 10 066449 | | 3/1998 |
| JP | 11 164688 A | | 6/1999 |

* cited by examiner

*Primary Examiner*—Shaojia Anna Jiang
*Assistant Examiner*—Traviss McIntosh, III
(74) *Attorney, Agent, or Firm*—Young & Thompson

(57) ABSTRACT

This invention concerns the use of compounds selected among 1,4β-D-glucuronans, and/or glycuronic polysaccharides derived from polymers of formula (I), and whereof the number of saccharide units is less than about 30, and/or esters and/or ethers corresponding to polymers of formula (I) or said oligosccahride derivatives, as phytosanitary products in applications related to their activity for amplifying the 1,3β-D-glucanase enzyme, and/or the 1,4β-D-glucanase, and/or the xyloglucan endotransglycolase.

3 Claims, 1 Drawing Sheet

Figure 1:
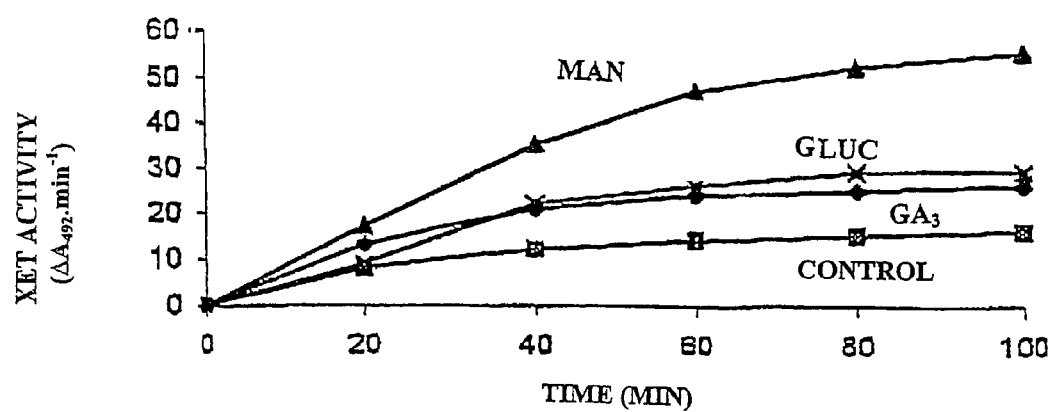

USE OF GLYCURONIC POLYSACCHARIDES AND OLIGOSACCHARIDES AS PHYTOSANITARY PRODUCTS AND/OR FERTILISER

The present invention concerns the use of 1,4β-D-glucuronan polymers and derived glycuronic oligosaccarides as phytosanitary products and/or fertilizers.

The enzyme 1,3-β-D-glucanase is a marker of defence mechanisms in plants. During reactions caused by hypersensitivity to a pathogen (bacteria, fungi, viruses), the plant reacts by inducing the synthesis of specific proteins named "PR-proteins" (Sintzi A. et al. (1993) Biochimie, 75, 687–706). These proteins, linked with pathogenesis, together with other molecules (such as salicylic acid) contribute to the development of resistance to the pathogen. Depending on their biochemical properties, and their physiological function, these proteins are listed in several groups. They share the following characteristics: low molecular weight, composition most often monomeric, resistance to proteolysis, stability in an acid medium or in extreme temperatures, their association with plasmic or endoplasmic membranes, and their parietal location. Amongst these PR proteins is Group 2, composed of 1,3β-D-glucanase enzymes, which recognize 1,3β-D-glucane chains as substrates. The role of these proteins in the defence of the plant is based on their capacity to lyse the walls of pathogens which are rich in 1,3β-D-glucanes (Boller T. (1993) In Mechanisms of Plant Defenses Responses. Fritig B. Legrand M. eds. Kluwer. Acadamic Publishers Dordrecht, 391–400).

However, this enzyme activity is not only involved in the defence of plants. In fact it can be regulated by phytohormones and it can be induced at certain stages of development of the plant. On this basis the enzyme 1,3-β-D-glucanase is a marker of growth and/or cell differentiation in plants.

This enzyme, like a number of PR-proteins (protease inhibitors, chitinases, proteins regulating the expression of genes encoding osmotin) are associated with growth and/or cell differentiation or with processes of adaptation to the environment. Some of these proteins are recognized by antibodies directed against 1,3-β-D-glucanases isolated from tobacco contaminated with tobacco mosaic (Kauffmann et al. (1990) Plant Mol. Biol. 14 (3): 381–90).

Activities of 1,3-β-D-glucanase or genes encoding these proteins are induced in the course of germination, and development of the flower buds and fruits (del Campillo E., Lewis L. N. (1992) Plant Physiology 99, 1015–1020; Neale et al. (1990) Plant Cell 2, 7, 673–684). In particular, these responses develop in the tissues by means of catabolic modifications (endosperm, pollen tubes, stem abscission zones, peduncles etc.), or during the period of mitotic division (case of anthers, stigmas, stems). They are dependent on hormones (auxins, cytokinins in general, absisic acid in particular) and molecules such as ethylene, controlling the maturation of fruits, or salicylic acid, controlling flowering, are also inducers. Finally, 1,3β-D-glucanase enzymes have been recorded for functions of adaptation of the plant to cold and to raised ozone levels (Hincha et al. (1997) Plant physiology 114, 1077–1083).

The enzyme 1,4β-D-glucanase is a marker of growth and/or cell differentiation in plants. This enzyme recognizes as substrate, linear chains of glucanes linked at β (1,4). It can hydrolyse cellulose, β glucanes (1,4) (1,6), and xyloglucan. Thus, it plays a part in the ultrastructural modifications of the walls of plant cells during the growth process. Its induction and/or that of the specific genes is revealed during processes involving the lysis of plant cell walls, rupture of the anthers, abscission zones of fruits and flowers (Hayaschi T., Oshimi C. (1994) Plant Cell Physiology 35 (3), 419–424; Brummel D. A. et al. (1997) Plant Biol. Mol. 33, 1, 97–195). It is controlled by ethylene, by hormones such as abscisic acid or auxin.

Xyloglucan endotransglycolase activity induces the modification of the xyloglucans of plant cell walls in response to environmental stimuli such as mechanical pressure, wind, darkness, and thermal shocks (Xu et al. (1996) Plant J. 9 (6), 879–89; Antosiewicz et al. (1997), 115 (4), 1319–28).

The present invention arises from the inventors' demonstration of the fact that 1,4β-D-glucuronans and glycuronic oligosaccharides derived from the latter have activities amplifying the enzyme 1,3β-D-glucanase and/or the enzyme 1,4β-D-glucanase, and/or the enzyme xyloglucan endotransglycolase, and, on this basis, are described as "eliciting" compounds, which can be used within the framework of phytosanitary uses or fertilization.

1,4β-D-glucuronan polymers have already been described in the French patent FR-B-2 688 222 of 3 Mar. 1992, relating to areas of use totally different from those mentioned above for the present invention, i.e. in the domains of food, pharmaceuticals, human or veterinary therapy, cosmetics or water purification, in particular as a gelling, thickening, hydrating, stabilizing, chelating or flocculating agent, as well as in the preparation of oligosaccharides.

The present invention has the aim of providing compounds which can be used as "elicitors" included in the composition of fertilizers (manure, biological fertilizers or biofertilizers) and phytosanitary products.

One of the aims of the present invention is to provide new biofertilizers which can be used in particular as stimulants of nutrition in addition to or as a replacement for commercial products based on potash and nitrates which are toxic to the environment, and/or as regulators of one or more stages of development of the plants.

Another aim of the present invention is to provide new phytosanitary products which can be used in particular as activators of defence and resistance reactions against biotic or abiotic stresses in addition to or as a replacement for pesticides which are toxic to the environment.

The present invention has as its subject the use of compounds chosen from:

1,4β-D-glucuronan polymers of formula (I) below:

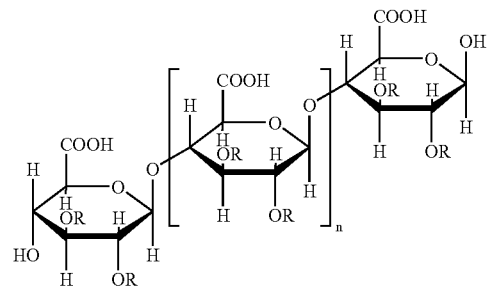

in which n is an integer which may be as great as approximately 2500, advantageously n is between approximately 300 and approximately 2500, and R represents H or COCH$_3$.

and/or the β(1–4) chain glycuronic oligosaccharides derived from polymers of formula (I), and of which the number of saccharidic units is less than approximately 30, and preferably between 2 and 15, and/or the esters and/or ethers corresponding to polymers of formula (I) or to the above mentioned oligosaccharidic derivatives, as phytosanitary products within the framework of uses linked to their activity of amplifying the enzyme 1,3β-D-glucanase, and/or as biofertilizers within the framework of uses linked to their activity of amplifying the enzyme 1,3β-D-glucanase, and/or the enzyme 1,4β-D-glucanase, and/or xyloglucan endotransglycolase.

Of the plants which can be treated within the framework of the present invention, the following may be cited: vines, fruit trees, cereals and market garden produce, or any other plant of economic interest.

The invention has more particularly as its subject the above mentioned use of compounds chosen from those cited above, as phytosanitary products within the framework of uses linked to their activity of amplifying the enzyme 1,3β-D-glucanase, such as the protection of plants against pathogens or predators, notably against bacteria, viruses, fungi, insects, nematodes, or the adaptation of plants to an abiotic stress, in particular adaptation to cold, or to raised ozone levels.

The invention has more particularly as its subject the use, as phytosanitary products, of 1,4β-D-glucuronan polymers of formula (I) in which n is an integer between approximately 300 and approximately 2500, and R represents H.

The invention also has more particularly as its subject the use, as phytosanitary products, of 1,4β-D-glucuronan polymers of formula (I) in which n is an integer between approximately 300 and approximately 2500, R represents H or COCH$_3$, the weight percentage of COCH$_3$ preferably being between 0 and 30.5.

The invention also concerns the use, as phytosanitary products, of β(1–4) chain glycuronic oligosaccharides, such as the oligo 1,4β-D-glucuronans, the oligo 1,4β-D-mannuronans, and the oligo 1,4β-D-guluronans, whose DP (degree of polymerization) is less than 30, and preferably between 2 and 15.

In the following, the expression "oligosaccharides with a degree of polymerization x (DPx)" shall be understood as meaning oligosaccharides made up of the same number x of saccharidic units, and the expression "oligosaccharides with an average degree of polymerization x (average DP x)" shall be understood as meaning oligosaccharides made up of a variable number of saccharidic units, whose average corresponds to x.

Glycuronic oligosaccharide derivatives preferred as phytosanitary products are chosen from the following:

the oligo 1,4β-D-glucuronans of DP8, and of average DP 8 the oligo 1,4β-D-mannuronan of DP4, the oligo 1,4β-D-guluronan of DP4.

The invention also has as its subject a process for the treatment of plants with 1,4β-D-glucuronan polymers and/or glycuronic oligosaccharides as defined above, with a view to obtaining plants resistant to the above mentioned pathogens, or adapted to an abiotic stress, notably the cold, or raised ozone levels.

The invention also concerns the use of compounds chosen from those cited above, as biofertilizers within the framework of uses linked to their activity of amplifying the enzyme 1,3β-D-glucanase, and/or the enzyme 1,4β-D-glucanase and/or the enzyme xyloglucan endotransglycolase.

The invention has more particularly as its subject the above mentioned use of oligo 1,4β-D-glucuronans, whose DP is below 30, and preferably between 2 and 15, as biofertilizers within the framework of uses linked to their activity of amplifying the enzyme 1,3β-D-glucanase, and/or the enzyme 1,4β-D-glucanase, notably within the framework of control of one or more stages of plant development, such as the control of fruit maturation, abscission, growth of the pistil or maturation of the anthers.

The invention has still more particularly as its subject the above mentioned use of oligo 1,4β-D-glucuronans of DP8 and average DP 8, as biofertilizers.

The invention has more particularly as its subject the above mentioned use of oligo 1,4β-D-mannuronans, whose DP is below 30, and preferably between 2 and 15, as biofertilizers within the framework of uses linked to their activity of amplifying the enzyme xyloglucan endotransglycolase, notably within the framework of control of the organization of cell walls during expansion of the tissues (vascular zones or parenchyma) of certain organs such as hypocotyls, cotyledons, leaves, pollen tubes, and fruits, and to reinforce the plant cell walls and adapt them to environmental stimuli such as wind, thermal or water shock, or mechanical pressure.

The invention also has as its subject a process for the treatment of plants with glycuronic oligosaccharides as defined above, with a view to obtaining plants in which one or more stages of development, such as fruit maturation, abscission, growth of the pistil or maturation of the anthers, are controlled over time.

The invention also has as its subject a process for treatment of plants with glycuronic oligosaccharides as defined above, with a view to obtaining plants, in which the organization of cell walls during expansion of the tissues is controlled, and in which the plant cell walls are reinforced to adapt them to environmental stimuli such as wind, thermal or water shock, or mechanical pressure.

The invention also concerns phytosanitary products and/or biofertilizers characterized in that they include at least one compound chosen from:

1,4β-D-glucuronan polymers of formula (I) mentioned above, in which n is an integer between approximately 300 and approximately 2500, and R represents H or COCH$_3$, and/or β(1–4) chain glycuronic oligosaccharides derived from polymers of formula (I), and of which the number of saccharidic units is less than approximately 30, and/or the esters and/or ethers corresponding to polymers of formula (I) or to the above mentioned oligosaccharidic derivatives.

The invention has more particularly as its subject phytosanitary products comprising at least one 1,4β-D-glucuronan polymer of formula (I) in which n is an integer between approximately 300 and approximately 2500, and R represents H.

The invention also concerns phytosanitary products comprising at least one 1,4β-D-glucuronan polymer of formula (I) in which n is an integer between approximately 300 and approximately 2500, R represents H or COCH$_3$, the percentage of COCH$_3$ by weight being preferably between 0 and 30.5.

The invention also has as its subject phytosanitary products, comprising at least one β(1–4) chain glycuronic oligosaccharide, such as the oligo 1,4β-D-glucuronans, the oligo 1,4β-D-mannuronans, and the oligo 1,4β-D-guluronans, whose DP is less than 30, and preferably between 2 and 15.

The invention has more particularly as its subject, phytosanitary products comprising at least one glycuronic oligosaccharide derivative chosen from the following:

the oligo 1,4β-D-glucuronans of DP8, and of average DP 8 the oligo 1,4β-D-mannuronan of DP4, the oligo 1,4β-D-guluronan of DP4.

The invention concerns more particularly biofertilizers comprising at least one oligo 1,4β-D-glucuronan whose DP is below approximately 30, and preferably between 2 and 15, and, preferably, biofertilizers comprising oligo 1,4β-D-glucuronans of DP8, and of average DP 8.

The invention concerns still more particularly biofertilizers comprising at least one oligo 1,4β-D-mannuronan whose DP is below approximately 30, and preferably between 2 and 15, and, preferably, biofertilizers comprising the oligo 1,4β-D-mannuronan of DP4.

The invention will be further described by means of the following detailed description of the preparation of 1,4β-D-glucuronan polymers and glycuronic oligosaccharides derived according to the invention, as well as the demonstration of their properties of amplifying the enzyme 1,3β-D-glucanase and/or the enzyme 1,4β-D-glucanase.

A) Preparation of Uronic Polymers and/or Their Oligosaccharides 1,4β-D-glucuronan polymers are obtained using fermentation processes of strains of bacteria isolated from the rhizosphere (*Rhyzobium, Sinorhyzobium, Agrobacterium, Pseudonomas, Burkolderia* etc.) which may or may not be modified by chemical mutations and/or genetic manipulations.

1,4β-D-glucuronan polymers can thus be obtained by selective oxidation of cellulose according to the processes described in various articles (Painter T. J., 1977, Preparation and periodate oxidation of C-6-oxycellulose: conformational interpretation of hamlacetal stability. Carbohy. Res. 55, 95–103; Chang P. S. and Robyt J. F., Oxidation of primary alcohol groups of naturally occurring polysaccharides with 2,2,6,6-tetramethyl-1-piperidine oxoammonium ion. J. Carbohydr. Chem., 15, 819–830; Isogai, A. and Kato, Y., 1998, Preparation of polyuronic acid from cellulose by TEMPO-mediated oxidation, Cellulose, 5, 153–164).

If necessary, the polymers thus obtained are modified and/or degraded by chemical and/or enzymatic means, during fermentation or by post-fermentation treatments.

1,4β-D-Glucuronan Polymer

By way of illustration, 1,4β-D-glucuronan polymer is obtained by fermentation of a mutated strain of *Rhizobium meliloti*, according to the protocol described in the French patent FR-B-2 688 222 of 3 Mar. 1992.

1,4β-D-Glucuronan Oligomer of Average DP 8

The previous native polymer, i.e. comprising at least 50% acetylated glucuronic units at C2 and at C3, is subjected to enzymatic hydrolysis. The enzyme is a glucuronate lyase of various origins, notably extracted from the pancreas of ormers, or of fungal origin (Dantas L. et al., Carbohydr. Res., 265 (1994) 303–310) or a glucuronate lyase present in the culture medium of bacteria such as strains of Rhizobiaceae (Michaud P., et al., Int. J. Hiol. Macromol. 21 (1997) 3–9). The mixture of oligosaccharides thus obtained is deacylated by a basic process (NaOH 0.1M), then fractionated on the basis of the degree of polymerization (DP) by gel-permeation chromatography using a BioGel P6 column (Dantas L. et al., mentioned above).

1,4β-D-Mannuronan and 1,4β-D-Guluronan Oligomers of DP 4

The starting polymer is an alginate, linear copolymer of mannuronic (M) and guluronic (G) acids, whose M/G ratio and mode of arrangement depend on the origin. The alginate is chosen on the basis of the type of oligomers to be prepared. Hydrolysis is carried out by enzymatic means: an alginate-lyase of ormer origin for the oligo-1,4β-D-mannuronans (Heyraud A. et al., Carbohydr. Res., 291 (1996) 115–126), an alginate-lyase of bacterial origin for the oligo-1,4β-D-guluronans (Patent FR 97 03218 of 11 Mar. 1997). The different oligosaccharides, separated according to DP by gel-permeation chromatography, are then purified depending on their structure by ionic chromatography in high-pressure liquid chromatography according to the process described in the article by Heyraud et al., mentioned above.

B) 1,3β-D-Glucanase Response Induced in the Protoplasts of *Rubus*

Experimental conditions: (1) preparation of protoplasts from cell suspensions of *Rubus fruticosus* L.; (2) incubation, or not, of n samples of $2.10^6$ protoplasts in the presence of "elicitors" (1,4-D-glucuronan polymers and 1,4β-D-galacturonan (400 μg/L) polymers, 1,4β-D-glucuronan oligomers of average DP 8, 1,4β-D-mannuronan oligomers of DP 4, and 1,4β-D-guluronan oligomers of DP 4 (50 nM)); (3) after 20 minutes, the protoplasts whether may be treated or not, are subjected to enzymatic extraction. 2 μg of proteins are used per enzymatic test, and per incubation period. The viability of the protoplasts is maintained at 95% for an experimental period of 6 hours; the Evans blue viability test used verifies the integrity of the plasmalemma.

Methodology: measurement of activity (1,3β-D-glucanase) is based on the calorimetric dosage (ferricyan test) of the substrate-reducing units (reduced hexamer from laminarin) released during hydrolysis. Based on the kinetics developed, curves are traced whose equations make it possible to calculate the speed of the enzymatic reaction. 2 kinetics, at least, are developed per sample, and per experimental "set". In general, at least 8 kinematics from samples of 2 independent "sets" are developed.

Results: the enzymatic activation elicited in the protoplasts is expressed as a % of the activity in the controls. The results are summarized in Table 1.

TABLE 1

| "elictor" | activity (% control) |
|---|---|
| a | 145 |
| b | 128 |
| c | 100 |
| d | 122 |
| e | 146 |

Table 1: Comparative analysis of the responses (1,3-β-D-glucanase) induced by the "elicitor" (1,4β-D-glucuronan polymer (400 μg/L) (a), oligo 1,4-β-D-glucuronan of average DP 8 (50 nM) (b), 1,4-β-D-galacturonan (400 μg/L) (c), oligo 1,4-β-D-mannuronan of DP 4 (50 nM) (d), oligo 1,4-β-D-guluronan of DP 4 (50 nM) (e).

Electrophoretic analysis by SD S-PAGE of the proteins making up the enzymatic extracts has been carried out. The marking of proteins on prints by a serum recognizing 1,3-β-D-glucanases isolated from tobacco contaminated with tobacco mosaic (Ori et al. (1990) EMBO J., 9 (11), 3429–36) confirms the presence of PR proteins.

The 1,4-β-D-glucuronan oligomer of average DP 8 and the polyglucuronan, used at a nanomolar concentration, in 20 minutes amplify by a factor of 1.5 and 1.3 respectively the 1,3-β-D-glucanase activity in plant protoplasts. Amongst the other products tested, oligo 1,4-β-D-guluronan of DP4 was the most effective.

C) 1,4-D-Glucanase Response Induced in Protoplasts of *Rubus*

Experimental elicitation conditions: identical to those reported above.

Methodology: measurement of activity (1,4β-D-glucanase) is based on the calorimetric dosage (ferricyan test) described above of the substrate-reducing units (reduced cellopentaose) released during hydrolysis.

Results: The results are shown in Table 2.

TABLE 2

| "elictor" | activity (% control) |
|---|---|
| a | 100 |
| b | 120 |
| c | 100 |
| d | — |
| e | 101 |

Table 2: Comparative analysis of the responses (1,4β-D-glucanase) induced by the "elicitor" (1,4β-D-glucuronan polymer (400 μg/L) (a), oligo 1,4β-D-glucuronan of average DP 8 (50 nM) (b), 1,4β-D-galacturonan polymer (400 μg/L) (c), oligo 1,4β-D-mannuronan of DP 4 (50 nM) (d), oligo 1,4β-D-guluronan of DP 4 (50 nM) (e).

The 1,4-β-D-glucuronan oligomer of average DP 8 used at a nanomolar concentration, in 20 minutes amplifies by a factor of 1.2 the 1,4β-D-glucanase activity in plant protoplasts.

D) Xyloglucan Endotransglycolase Response Induced in Protoplasts of *Rubus*

Experimental elicitation conditions. $2.10^6$ protoplasts in 1 ml Tris-HCl buffer (pH 4.8) are incubated in the presence, or not, of an elicitor (50 nM) or of a hormone (50 nM): mannuronan oligomer of DP4 or glucuronan oligomer of DP8 or gibberellin $GA_3$. After 20, 40, 60, 100 and 120 minutes of interaction, the protoplasts are recovered by centrifugation, then subjected to enzymatic extraction.

Methodology: measurement of XET activity is carried out in the wells of microtitration plates in 4 stages. Stage 1: immobilization of the acceptor, i.e. the neoglycoprotein XXLG≈BSA. Stage 2: introduction of the reaction medium (XET enzymatic extraction (equivalent to 1 μg of proteins) substrate marked DIG, i.e. XG≈DIG in the Tris-HC1 buffer, pH=7, 25 mM). Stage 3: immunomarking according to the anti-DIG marked peroxydase sequence, anti-peroxydase marked peroxydase. Stage 4: dosage of the peroxydase activity in a citrate-phosphate buffer (50 nM, pH 5.5).

The peroxydase activity is measured at 492 nm. At least 3 curves of peroxydase activity are traced per experimental condition, and the experiments are carried out using 3 protoplast suspensions. The XET activity is measured by the slope (ΔA 492) of the curve deduced by linear regression from 9 peroxydase kinetics curves.

Abbreviations:
DIG: digoxygenin
XET: xyloglucan endotransglycolase—XG: xyloglucan polymer—XXLG: non-fucosylated xyloglucan oligomer.

Results: The results are indicated in FIG. 1.

The mannuronan oligomer of DP4 (MAN) induces the strongest XET response (amplification in 20 minutes by a factor or 2.12); the glucuronan oligomer of DP8 (GLUC) and the hormone (GA3) are less effective (amplification in 20 minutes by a factor of 1.62 and 1.12 respectively). The reference XET activity is that of the non-elicited protoplasts (CONTROL).

Legend to FIG. 1: XET activity is indicated on the Y-axis, and time on the X-axis; the curve following the triangles corresponds to the results obtained with the mannuronan oligomer of DP4 (MAN), the curve following the crosses corresponds to the results obtained with the glucuronan oligomer of DP8 (GLUC), the curve following the circles corresponds to the results obtained with the hormone (GA3), the curve following the squares corresponds to the results obtained with the control.

What is claimed is:

1. A phytosanitary method for the protection of plants against pathogens or predators and/or for facilitating the adaptation of plants to raised ozone levels, comprising applying to said plants a 1,3β-D-glucanase amplifying effective amount of oligo 1,4β-D-mannuronans of DP 4.

2. A method for controlling abscission, controlling growth or maturation of a pistil or anthers, controlling organization of cell walls during expansion of tissues and/or reinforcing plant cell walls and adapting them to environmental stimuli, comprising applying to plants a 1,3β-D-glucanase/1,4β-D-glucanase/xyloglucan endotransglycolase amplifying effective amount of oligo 1,4β-D-mannuronans of DP 4.

3. A phytosanitary method for the protection of plants against pathogens or predators and/or facilitating the adaptation of plants to raised ozone layers, comprising applying to said plants a composition comprising a fertilizer and an amplifying effective amount of an eliciting compound consisting of oligo 1,4β-D-mannuronans of DP 4.

* * * * *